(12) United States Patent
Uematsu et al.

(10) Patent No.: US 11,649,205 B2
(45) Date of Patent: May 16, 2023

(54) VINYLSULFONIC ANHYDRIDE, METHOD FOR PRODUCING SAME, AND METHOD FOR PRODUCING VINYLSULFONYL FLUORIDE

(71) Applicant: ASAHI KASEI KABUSHIKI KAISHA, Tokyo (JP)

(72) Inventors: Nobuyuki Uematsu, Tokyo (JP); Hideki Date, Tokyo (JP); Yasuhiro Nagato, Tokyo (JP); Akitake Nakamura, Tokyo (JP); Kenichi Yakigaya, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 195 days.

(21) Appl. No.: 17/055,124

(22) PCT Filed: Jun. 20, 2019

(86) PCT No.: PCT/JP2019/024582
§ 371 (c)(1),
(2) Date: Nov. 13, 2020

(87) PCT Pub. No.: WO2020/012913
PCT Pub. Date: Jan. 16, 2020

(65) Prior Publication Data
US 2021/0269395 A1    Sep. 2, 2021

(30) Foreign Application Priority Data

Jul. 9, 2018 (JP) .............................. JP2018-130067
Jul. 30, 2018 (JP) .............................. JP2018-142448

(51) Int. Cl.
| | |
|---|---|
| *C07C 309/10* | (2006.01) |
| *C07C 303/22* | (2006.01) |
| *C07C 303/28* | (2006.01) |
| *C07C 303/32* | (2006.01) |
| *C07C 309/65* | (2006.01) |
| *C07C 309/66* | (2006.01) |
| *C07C 309/80* | (2006.01) |

(52) U.S. Cl.
CPC .......... *C07C 309/10* (2013.01); *C07C 303/22* (2013.01); *C07C 303/28* (2013.01); *C07C 303/32* (2013.01); *C07C 309/65* (2013.01); *C07C 309/66* (2013.01); *C07C 309/80* (2013.01)

(58) Field of Classification Search
USPC ........................................................ 562/110
See application file for complete search history.

(56) References Cited

U.S. PATENT DOCUMENTS

| 3,560,568 A | 2/1971 | Resnick |
| 5,285,002 A | 2/1994 | Grootaert |
| 2008/0004473 A1 | 1/2008 | Sugiyama et al. |

FOREIGN PATENT DOCUMENTS

| CN | 101052616 A | 10/2007 |
| EP | 0041738 A1 | 12/1981 |
| JP | S5728024 A | 2/1982 |
| JP | 2010218982 A | 9/2010 |
| JP | 2015224218 A | 12/2015 |
| RU | 2131888 C1 | 6/1999 |

OTHER PUBLICATIONS

Japan Society for the Promotion of Science, Introduction to Fluorine Chemistry 2010: The Frontiers of Basics and Applications, Fluorine Chemistry 155th Commission, Apr. 2010, pp. 353-355 with a partial English translation.
Oliver Gronwald et al., Synthesis of difluoroethyl perfluorosulfonate monomer and its application, Journal of Fluorine Chemistry, Jun. 2008, pp. 535-540, vol. 129, Issue 6.
Sep. 3, 2019, International Search Report issued in the International Patent Application No. PCT/JP2019/024582.
Jan. 12, 2021, International Preliminary Report on Patentability issued in the International Patent Application No. PCT/JP2019/024582.
Aug. 31, 2021, the Supplementary European Search Report issued by the European Patent Office in the corresponding European Patent Application No. 19834126.5.

*Primary Examiner* — Ana Z Muresan
(74) *Attorney, Agent, or Firm* — Kenja IP Law PC

(57) ABSTRACT

The present disclosure is directed to provide a vinylsulfonic anhydride which is useful as a synthetic intermediate for synthesis of a fluorinated monomer. It is also directed to efficiently produce the vinylsulfonic anhydride. It is further directed to efficiently produce a fluorinated monomer using the vinylsulfonic anhydride. A vinylsulfonic anhydride of the present disclosure is expressed by the general formula (1). Further, a process for producing a vinylsulfonic anhydride of the present disclosure includes making a vinylsulfonic acid compound represented by the general formula (2) come in contact and be mixed with an anhydridization agent. Further, a process for producing a vinylsulfonyl fluoride of the present disclosure includes a step (b) of making a vinylsulfonic anhydride represented by the general formula (1) come in contact and be mixed with a fluorinating agent to prepare a reaction mixture including a vinylsulfonyl fluoride represented by the general formula (3) and a vinylsulfonic acid compound represented by the general formula (2).

10 Claims, No Drawings

VINYLSULFONIC ANHYDRIDE, METHOD FOR PRODUCING SAME, AND METHOD FOR PRODUCING VINYLSULFONYL FLUORIDE

TECHNICAL FIELD

The present disclosure relates to a vinylsulfonic anhydride, a process for producing the same, and a process for producing a vinylsulfonyl fluoride. More particularly, the present disclosure relates to a vinylsulfonic anhydride which is useful as a synthetic intermediate for synthesis of a fluorinated monomer which may serve as a raw material of fluorine-based polymer electrolytes, such as membranes for fuel cells, catalyst binder polymers for fuel cells, and membranes for chlor-alkali electrolysis; to a process for producing such a vinylsulfonic anhydride; and to a process for producing a fluorinated monomer using the vinylsulfonic anhydride.

BACKGROUND

Fluorine-based polymer electrolytes represented by the following general formula (5) have been typically used as main components of membranes for fuel cells, catalyst binder polymers for fuel cells, membranes for chlor-alkali electrolysis, and the like:

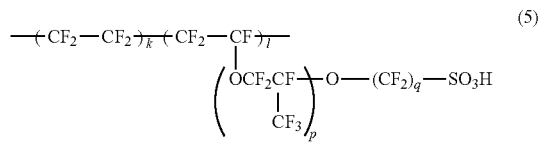
(5)

(wherein p is an integer from 0 to 6, and q is an integer from 1 to 6).

It is well known that a fluorine-based polymer electrolyte represented by the general formula (5) can be produced by subjecting a copolymer of a fluorinated monomer represented by the following general formula (6) and tetrafluoroethylene (TFE) to saponification and acid treatment:

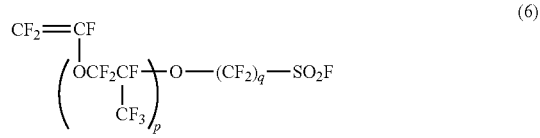
(6)

(wherein p and q are as defined in the general formula (5)).

Among fluorinated monomers represented by the general formula (6), fluorine-based polymer electrolytes produced from monomers where p is 1 and q is from 2 to 4 have been widely used. It is well known that monomers where p is 1 and q is from 2 to 4 can be produced, for example, via the following route:

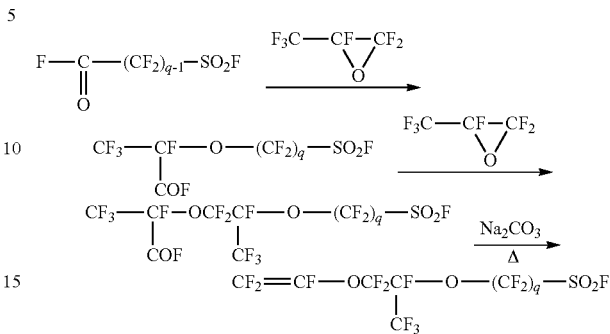

In the meantime, it is well known that fluorine-based polymer electrolytes where p is 0 in the general formula (5) have shorter spacer portions between the main chain and sulfonic acid groups than those in polymers where p is 1 or more, and thus have higher glass transition temperatures and higher mechanical strengths than polymers where p is 1 or more.

However, syntheses of fluorinated monomers represented by the general formula (6) which serve as raw materials of such fluorine-based polymer electrolytes are difficult when p is 0, which has posed a challenge. More specifically, when $CF_3CF(COF)O(CF_2)_qSO_2F$ is subjected to decarboxylation and vinylation similarly to the above-mentioned reaction where p is 1 or more in an attempt to synthesize a fluorinated monomer where p is 0 in the general formula (6), cyclization becomes dominant. As a result, the yield of the fluorinated monomer of interest having the short chain structure where p is 0 is known to be extremely low. For example, when q is 2, only cyclization proceeds, making production of the fluorinated monomer difficult (see NPL 1, for example).

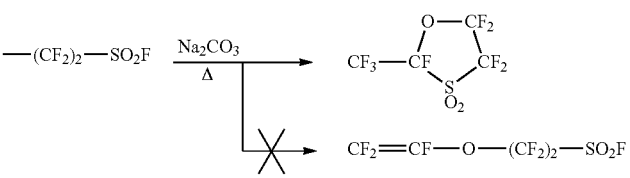

As another process for synthesizing a fluorinated monomer where p is 0 in the general formula (6), a synthesis process using a chlorine atom-containing fluoroepoxide is disclosed (see PTL 1, for example). This process, however, is far from practical because it needs a special chlorine atom-containing fluoroepoxide which is not widely available and synthesis of which is cumbersome.

A still another process for synthesizing a fluorinated monomer where p is 0 in the general formula (6) is disclosed (see PTL 2, for example). More specifically, a 5-membered cyclic compound is produced through decarboxylation of $CF_3CF(COF)O(CF_2)_2SO_2F$ by heating with sodium carbonate. The 5-membered cyclic compound is then subjected to a reaction with sodium methoxide (NaOCH$_3$) to yield $CF_2=CFO(CF_2)_2SO_3Na$, which is then subjected to a reaction with phosphorus pentachloride (PCl$_5$) to yield $CF_2=CFO(CF_2)_2SO_2Cl$, followed by a reaction with sodium fluoride (NaF) to yield a fluorinated monomer ($CF_2=CFO(CF_2)_2SO_2F$) having p of 0 and q of 2 in the general formula (5).

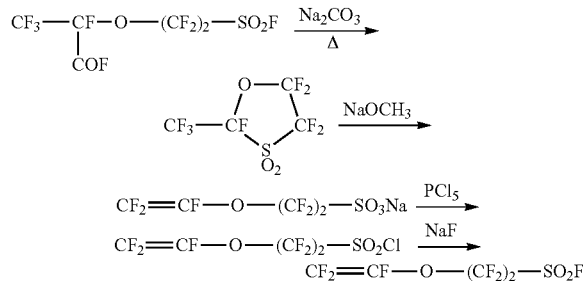

CITATION LIST

Patent Literature

PTL 1: JPS57-28024A
PTL 2: U.S. Pat. No. 3,560,568B

Non-Patent Literature

NPL 1: The 155$^{th}$ Committee on Fluorine Chemistry, Japan Society for the Promotion of Science, "Introduction to Fluorine Chemistry 2010: The Frontiers of Basics and Applications," April 2010, pp. 353-355.
NPL 2: Gronwald, Oliver, et al. "Synthesis of difluoroethyl perfluorosulfonate monomer and its application." *Journal of Fluorine Chemistry* 129 (2008) 535-540.

SUMMARY

Technical Problem

When $CF_2=CFO(CF_2)_2SO_3Na$ is mixed with phosphorus pentachloride and heated, however, by-products of phosphorus oxychloride ($POCl_3$) and sodium chloride (NaCl) are produced, together with $CF_2=CFO(CF_2)_2SO_2Cl$ as the target product:

$CF_2=CFO(CF_2)_2SO_3Na+PCl_5 \rightarrow$
$CF_2=CFO(CF_2)_2SO_2Cl+POCl_3+NaCl$.

PTL 2 discloses a process for producing a fluorinated monomer ($CF_2=CFO(CF_2)_2SO_2F$) by preparing a mixture of $CF_2=CFO(CF_2)_2SO_2Cl$ and phosphorus oxychloride as a distilled fraction, which is then subjected to a reaction with sodium fluoride. However, this process is far from upgradable to industrial scales for the following reasons. When sodium fluoride and $CF_2=CFO(CF_2)_2SO_2Cl$ are subjected to a reaction in the presence of phosphorus oxychloride, production of a fluorinated monomer may be inhibited by the influence of highly reactive phosphorus oxychloride. Further, phosphorus oxychloride may restrict reaction conditions such as the solvent used during the reaction and the reaction temperature. Thus, cumbersome procedures are required for separating and removing phosphorus oxychloride from the mixture. Against the background, there has been a demand for developing a new process which enables efficient production of fluorinated monomers without using phosphorus pentachloride.

Solution to Problem

Having intensively studied solutions to the aforementioned problems, we discovered that a fluorinated monomer and a vinylsulfonic acid compound were produced by making a vinylsulfonic anhydride produced from the vinylsulfonic acid compound and an anhydridization agent come in contact and be mixed with a fluorinating agent, to thereby found that the vinylsulfonic anhydride serves a key synthetic intermediate which derives the fluorinated monomer. In addition, we also discovered that the vinylsulfonic acid compound isolated from a reaction mixture of the fluorinated monomer and the vinylsulfonic acid compound could be converted by the anhydridization agent back to the vinylsulfonic anhydride, which can be reused as the synthetic intermediate deriving the fluorinated monomer, thereby completing the present disclosure.

Specifically, the present disclosure provides the following.

[1] A vinylsulfonic anhydride represented by the following general formula (1):

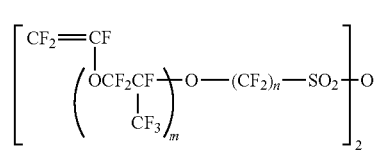

(where m is an integer from 0 to 3, and n is an integer from 1 to 6).

[2] A process for producing a vinylsulfonic anhydride represented by the following general formula (1):

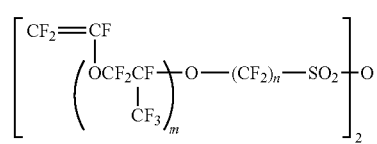

(where m is an integer from 0 to 3, and n is an integer from 1 to 6),
the process comprising:
a step (a) of making a vinylsulfonic acid compound represented by the following general formula (2) come in contact and be mixed with an anhydridization agent:

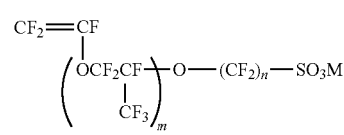

(where m represents an integer from 0 to 3, n represents an integer from 1 to 6, and M represents a hydrogen atom, an alkali metal, an alkaline earth metal, Ag, a quaternary ammonium salt, or a quaternary phosphonium salt).

[3] A process for producing a vinylsulfonyl fluoride comprising:
a step (b) of making a vinylsulfonic anhydride represented by the following general formula (1) come in contact and be mixed with a fluorinating agent:

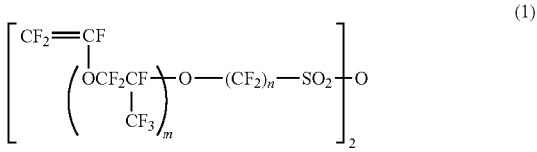

(1)

(where m is an integer from 0 to 3, and n is an integer from 1 to 6)

to prepare a reaction mixture comprising a vinylsulfonyl fluoride represented by the following general formula (3):

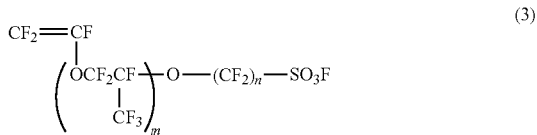

(3)

(where m is an integer from 0 to 3, and n is an integer from 1 to 6); and a vinylsulfonic acid compound represented by the following general formula (2):

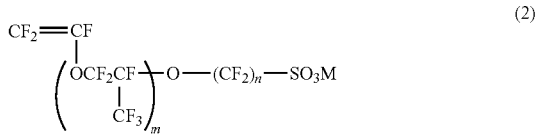

(2)

(where m represents an integer from 0 to 3, n represents an integer from 1 to 6, and M represents a hydrogen atom, an alkali metal, an alkaline earth metal, Ag, a quaternary ammonium salt, or a quaternary phosphonium salt).

[4] The process for producing a vinylsulfonyl fluoride according to [3], wherein the vinylsulfonic anhydride is a vinylsulfonic anhydride produced by the process for producing a vinylsulfonic anhydride according to [2].

[5] The process for producing a vinylsulfonyl fluoride according to [3] or [4], further comprising a step (c) of separating the vinylsulfonyl fluoride represented by the general formula (3) and the vinylsulfonic acid compound represented by the general formula (2), from the reaction mixture prepared in the step (b).

[6] The process for producing a vinylsulfonic anhydride according to [2], wherein the step (a) comprises making the vinylsulfonic acid compound represented by the general formula (2) obtained in the step (c) according to [5], come in contact and be mixed with the anhydridization agent.

[7] The process for producing a vinylsulfonic anhydride according to [2] or [6], further comprising a step (d) of making a vinylsulfonic acid compound in which M in the general formula (2) is an alkali metal, an alkaline earth metal, Ag, a quaternary ammonium salt, or a quaternary phosphonium salt, come in contact and be mixed with an acidic substance, for conversion to a vinylsulfonic acid represented by the following general formula (4):

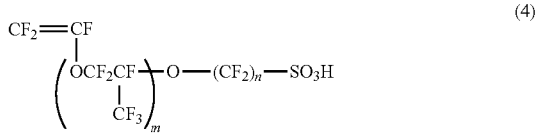

(4)

(where m and n are as defined in the general formula (2)).

[8] The process for producing a vinylsulfonyl fluoride according to any one of [3] to [5], wherein the fluorinating agent is one or more selected from the group consisting of hydrogen fluoride, a metal fluoride, a quaternary ammonium fluoride, and a quaternary phosphonium fluoride.

[9] The process for producing a vinylsulfonic anhydride according to any one of [2], [6], and [7], wherein the anhydridization agent is one or more selected from the group consisting of phosphorus pentoxide, acetic anhydride, trifluoroacetic anhydride, methanesulfonic anhydride, trifluoromethanesulfonic anhydride, p-toluenesulfonic anhydride, thionyl chloride, dicyclohexylcarbodiimide, cyanuric chloride, titanium tetrachloride, and benzenesulfonyl chloride.

[10] The process for producing a vinylsulfonic anhydride according to [2], wherein the step (a) comprising a step of separating the vinylsulfonic anhydride represented by the general formula (1).

[11] The process for producing a vinylsulfonic anhydride according to [10], further comprising a step of, after separating the vinylsulfonic anhydride represented by the general formula (1), collecting the vinylsulfonic acid compound represented by the general formula (2) from a resultant residue.

Advantageous Effect

According to the present disclosure, a vinylsulfonic anhydride can be provided which is useful as a synthetic intermediate for synthesis of a fluorinated monomer which may serve as a raw material of fluorine-based polymer electrolytes used for membranes for fuel cells, catalyst binder polymers for fuel cells, membranes for chlor-alkali electrolysis, and the like. Further, an efficient production of such a vinylsulfonic anhydride can be achieved, and this vinylsulfonic anhydride can be used for efficient production of a fluorinated monomer.

DETAILED DESCRIPTION

Hereinafter, an embodiment for embodying the present disclosure (hereinafter referred to merely as "the present embodiment") will be described in detail.

A vinylsulfonic anhydride of the present disclosure is a vinylsulfonic anhydride represented by the following general formula (1) (hereinafter may also be referred to as the "compound (1)"):

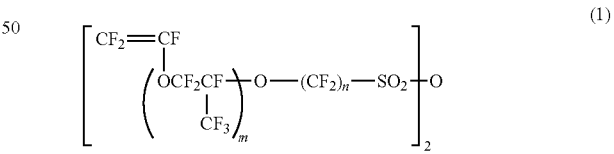

(1)

(where m is an integer from 0 to 3, and n is an integer from 1 to 6).

The compound (1) is a useful synthetic intermediate capable of deriving a vinylsulfonic acid compound represented by the later-mentioned general formula (2), as well as a vinylsulfonyl fluoride represented by the later-mentioned general formula (3).

In the compound (1), m is an integer from 0 to 3, and n is an integer from 1 to 6. From the viewpoint of the performances as raw material of fluorine-based polymer electrolytes, such as membranes for fuel cells, catalyst binder polymers for fuel cells, and membranes for chlor-alkali electrolysis, derived from a copolymer of a vinylsulfonyl fluoride represented by the following general formula (3) (fluorinated monomer) and TFE, and ease of synthesis of the vinylsulfonyl fluoride represented by the following general formula (3), m of an integer from 0 to 2 and n of an integer from 2 to 6 are preferred, m of an integer from 0 to 1 and n of an integer from 2 to 6 are more preferred, and m of an integer from 0 to 1 and n of an integer from 2 to 4 are the most preferred.

A process for producing a vinylsulfonic anhydride of the present disclosure includes a step (a) of making a vinylsulfonic acid compound represented by the following general formula (2) (hereinafter may also be referred to as the "compound (2)") come in contact and be mixed with an anhydridization agent:

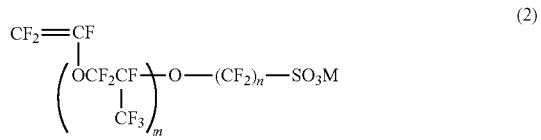

(where m represents an integer from 0 to 3, n represents an integer from 1 to 6, and M represents a hydrogen atom, an alkali metal, an alkaline earth metal, Ag, a quaternary ammonium salt, or a quaternary phosphonium salt).

The m and n in the compound (2) are the same as m and n in the compound (1) which is to be obtained by making the compound (2) come in contact and be mixed with an anhydridization agent.

A process for producing a vinylsulfonyl fluoride of the present disclosure includes a step (b) of making the compound (1) come in contact and be mixed with a fluorinating agent to prepare a reaction mixture including a vinylsulfonyl fluoride represented by the following general formula (3) (hereinafter may also be referred to as the "compound (3)"):

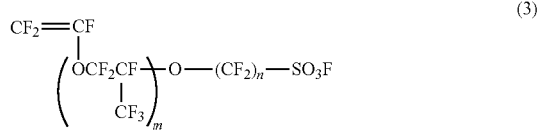

(wherein m and n are as defined in the general formula (1)); and the compound (2).

In the present disclosure, a step (c) of separating each of the compound (3) and the compound (2) from the reaction mixture containing the compound (3) and the compound (2) prepared in the step (b), is included. A copolymer produced from the compound (3) obtained in the step (c) and TFE can be used for production of fluorine-based polymer electrolytes, such as membranes for fuel cells, catalyst binder polymers for fuel cells, and membranes for chlor-alkali electrolysis. Further, the compound (2) produced in the step (c) is made to come in contact and be mixed with an anhydridization agent to produce the compound (1), which can be reused as the synthetic intermediate to derive the fluorinated monomer.

Further, in the present disclosure, in the case where M in the compound (2) is an alkali metal, an alkaline earth metal, Ag, a quaternary ammonium salt, or a quaternary phosphonium salt, a step (d) of making the compound (2) come in contact and be mixed with an acidic substance for conversion to a vinylsulfonic acid represented by the following general formula (4):

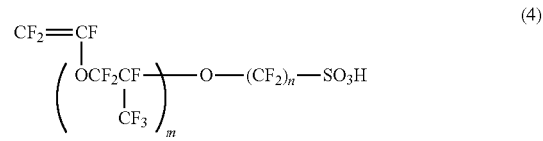

(where m and n are as defined in the general formula (2)), is included.

According to the process for producing a vinylsulfonyl fluoride of the present embodiment, the steps (a) to (d) enable the compound (2) to be used as a raw material for producing a compound (3) which is useful as a fluorine-based monomer, by way of the compound (1) as a useful synthetic intermediate of the present embodiment, as well as enabling the compound (2) to be collected for being reused.

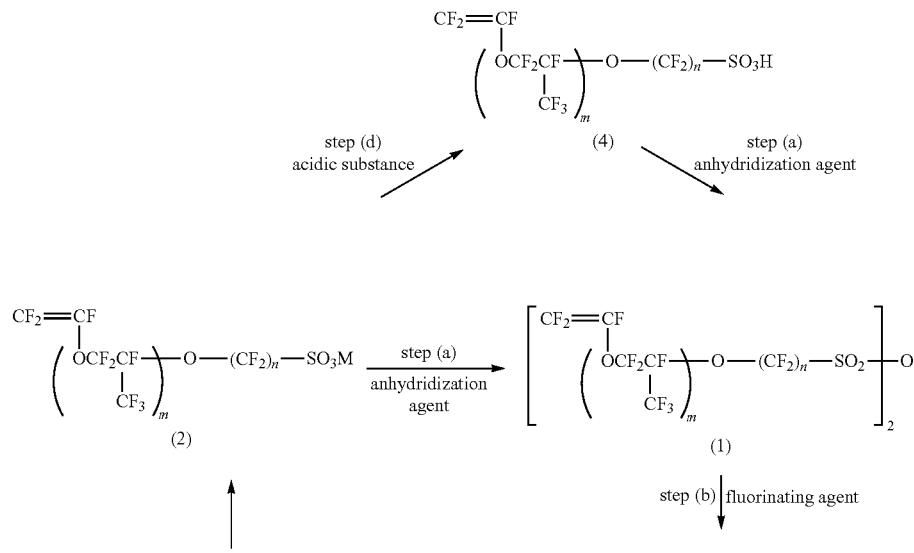

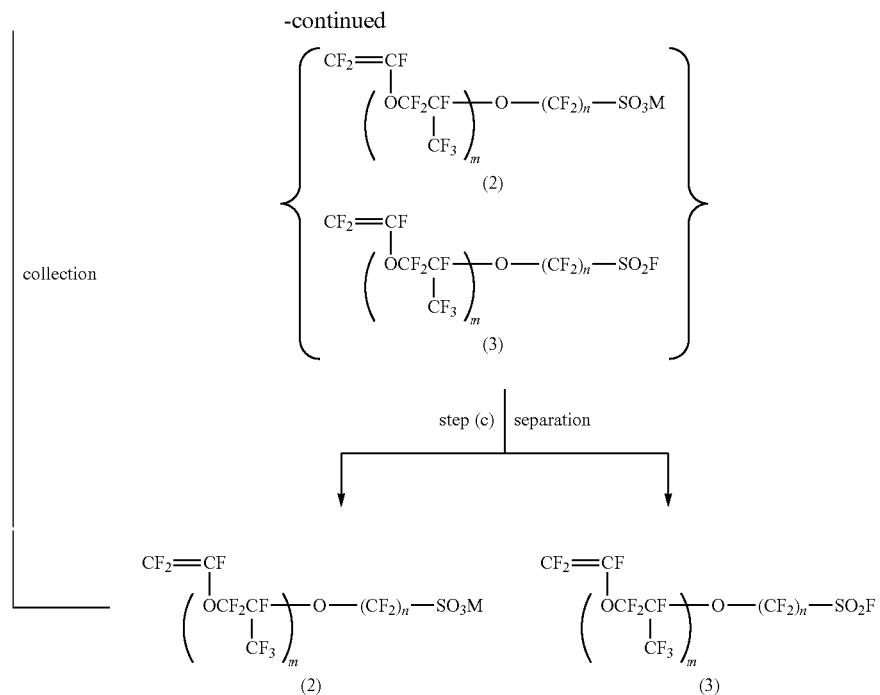

<Step (a)>

The step (a) is a step of producing a compound (1) from a compound (2) and an anhydridization agent.

The process for producing a vinylsulfonic anhydride of the present disclosure includes at least a step (a).

The technique to produce the compound (2) is not particularly limited, and a vinylsulfonic acid compound where m is 0 in the compound (2), for example, can be produced by subjecting $CF_3CF(COF)O(CF_2)_nSO_2F$ and sodium hydroxide to a reaction, followed by heating and decarboxylation to produce the compound (2) (see NPL 2, for example). We also discovered another process for producing a compound (2) by subjecting an alkaline metal carboxylate derived from $CF_3CF(COF)O(CF_2)_nSO_2F$ and sodium carbonate to thermal decomposition, followed by a reaction with a silanol compound. Further, as will be described later, a compound (2) can also be produced by subjecting a compound (1) to be reacted with a fluorinating agent (step (b)), and separating each of the compound (3) and the compound (2) which are produced.

Examples of the above-mentioned anhydridization agent include phosphorus pentoxide, acetic anhydride, trifluoroacetic anhydride, methanesulfonic anhydride, trifluoromethanesulfonic anhydride, p-toluenesulfonic anhydride, thionyl chloride, dicyclohexylcarbodiimide, cyanuric chloride, titanium tetrachloride, and benzenesulfonyl chloride. From the viewpoint of the availability and high controllability of the reaction, phosphorus pentoxide, trifluoroacetic anhydride, trifluoromethane sulfonic anhydride, thionyl chloride, cyanuric chloride, and titanium tetrachloride are preferred; phosphorus pentoxide, trifluoroacetic anhydride, trifluoromethanesulfonic anhydride, and thionyl chloride are more preferred; and phosphorus pentoxide or thionyl chloride is the most preferred. The above anhydridization agents may be used alone or in a combination of two or more.

The anhydridization agent is preferably used in the step (a) in an amount of 1 molar equivalent or more with respect to 1 mol of the compound (2). In order to achieve efficient usage of the anhydridization agent and to enhance the production yield of the compound (1), the anhydridization agent is used in an amount of preferably 1 to 20 molar equivalents, more preferably 1 to 10 molar equivalents, and particularly preferably 1 to 5 molar equivalents with respect to 1 mol of the compound (2).

In the step (a), the reaction may be carried out in the presence of a solvent or under a solvent-free condition.

In the case where the step (a) is carried out in the presence of a solvent, preferred solvents are solvents inert to the raw materials and the reaction products. Among these, a nitrile-based solvent and a fluorine-based solvent are suitably used.

Any of generally-used nitrile-based solvents can be used without any particular limitation, and examples of the nitrile-based solvent include alkylnitriles having at least one nitrile group as a substituent at a saturated hydrocarbon skeleton, such as acetonitrile, propionitrile, butyronitrile, and adiponitrile. These compounds may be used alone or in a combination of two or more. Among the nitrile-based solvents, acetonitrile and propionitrile are preferred, and acetonitrile is more preferred. This is because their lower boiling points are advantageous in making the step more cost effective, when solvent distillation is required at any stage or at two or more stages of before, during, and after the reaction. In addition, in the case where the reaction time can be shortened to thereby make the step more cost effective, a nitrile-based solvent having a high boiling point is preferably used for raising the reaction temperature, and adiponitrile is more preferred.

Any of generally-used fluorine-based solvents can be used without any particular limitation, and examples of the fluorine-based solvent include fluoroalkyl sulfonic anhydrides $(C_mF_{2m+1}SO_2)_2O$ (m=1-10), fluoroalkyl sulfonic acid esters $C_mF_{2m+1}SO_2OC_nF_{2n+1}$ (m=1-10 and n=1-10), perfluoroalkanes $C_mF_{2m+2}$ (m=4-20), perfluoroalkylamines $(C_mF_{2m+1})_3N$ (m=2-10), and perfluoropolyethers. From the viewpoint of ease of collection of the vinylsulfonic anhydride after the reaction, fluoroalkyl sulfonic anhydride, perfluoroalkanes, and perfluoropolyethers are particularly preferred. A solvent may be used alone, or two or more solvents may be used in a combination.

In the case where the step (a) is carried out in the presence of a solvent, the reaction temperature is typically from −40° C. to 250° C. From the viewpoint of the thermal stabilities of the compound (1) and the compound (2) and the production rate of the compound (1), the reaction temperature is preferably from −20° C. to 230° C., more preferably from 0° C. to 200° C., and particularly preferably from 10° C. to 150° C.

In the case where the step (a) is carried out in the presence of a solvent, the reaction time is typically 0.01 to 100 hours, and is preferably 0.1 to 80 hours.

In the case where the step (a) is carried out under a solvent-free condition, the reaction temperature is typically −40° C. to 300° C. From the viewpoint of the thermal stabilities of the compound (1) and the compound (2) and the production rate of the compound (1), the reaction temperature is preferably from −20° C. to 280° C., more preferably from 0° C. to 250° C., and particularly preferably from 10° C. to 200° C.

In the case where the step (a) is carried out under a solvent-free condition, the reaction time is typically from 0.01 to 200 hours, and is preferably from 0.1 to 180 hours.

The reaction atmosphere in the step (a) may be any of widely used atmospheres without any particular limitation, irrespective of whether the reaction is carried out under a solvent-free condition or in the presence of a solvent. The air atmosphere, a nitrogen atmosphere, an argon atmosphere, and the like are typically used. Among these, a nitrogen atmosphere and an argon atmosphere are preferred because formation of by-products by oxidation can be suppressed in some cases. Further, a nitrogen-atmosphere is more preferred because it tends to be excellent in cost effectiveness.

The reaction pressure in the step (a) is not particularly limited irrespective of whether the reaction is carried out under a solvent-free condition or in the presence of a solvent, and the reaction is carried out under the atmospheric pressure, an increased pressure, or a reduced pressure. In the case where a compound which may be volatile is present and preventing volatilization is desirable, an increased pressure higher than the atmospheric pressure is effective. In contrast, in the case where removing a volatile component from the mixture is desirable, a reduced pressure lower than the atmospheric pressure is effective.

In the step (a), any of generally-used contact and mixing techniques can be used without any particular limitation, irrespective of whether the reaction is carried out under a solvent-free condition or in the presence of a solvent. Exemplary techniques include techniques by means of an agitating blade (e.g., a fan, propeller, cross, butterfly, folding impeller, turbine, disc turbine, disper, paddle, inclined paddle, or screw blade); techniques by means of a grind machine (e.g., a jaw crusher, gyratory crusher, impact crusher, cone crusher, roll crusher, cutter mill, stamp mill, ring mill, roller mill, rotary mill, vibration mill, planetary mill, hammer mill, bead mill, attritor, or pin mill); and techniques by means of resonance (e.g., a resonant acoustic mixer). These techniques may be used alone or in a combination of two or more. In addition, a grinding medium generally used in a bead mill or the like may be used, such as alumina beads, glass beads, zirconia beads, zircon beads, and steel beads, because they can increase the efficiency of contact and mixing (and the beads may be balls). These grinding media may be used alone or in a combination of two or more.

Any of techniques for separating and collecting the compound (1) from the resultant reaction mixture in the step (a) may be used without any particular limitation, irrespective of whether the reaction is carried out under a solvent-free condition or in the presence of a solvent. Exemplary techniques include extracting the compound (1) from the reaction mixture using a solvent; and separating the compound (1) from the mixture during the reaction and/or after the reaction by distillation.

As the solvent to be added, solvents inert to the compound (1) are preferred. Among these, a nitrile-based solvent and a fluorine-based solvent are suitably used. Any of generally-used nitrile-based solvents can be used without any particular limitation, and examples of the nitrile-based solvent include alkylnitriles having at least one nitrile group as a substituent at a saturated hydrocarbon skeleton, such as acetonitrile, propionitrile, butyronitrile, and adiponitrile. Any of generally-used fluorine-based solvents can be used without any particular limitation, and examples of the fluorine-based solvent include perfluoroalkanes $C_mF_{2m+2}$ (m=4-20), perfluorobenzene, perfluorotoluene, perfluoro(2-butyltetrahydrofuran), 2H,3H-perfluoropentane, perfluoroalkylamines $(C_mF_{2m+1})_3N$ (m=2-10), and perfluoropolyethers. A solvent may be used alone, or two or more solvents may be used in a combination. These solvents may be used alone or in a combination of two or more.

In the case where the reaction is carried out in the step (a) under a solvent-free condition, for example, the compound (1) may be distilled out by distillation by heating the resultant reaction mixture while reducing the pressure inside the reactor system.

In the case where the reaction is carried out using a solvent in the step (a), for example, the compound (1) can be separated from the solvent by removing any insoluble components in the resultant reaction mixture by filtration or the like, and then heating the collected filtrate to distill out the solvent and the compound (1) by distillation. The separated solvent may be reused in the step (a).

After the compound (1) is separated and collected in the step (a), the compound (2) may be collected from the resultant residue. Any of collection techniques may be used without any particular limitation. Exemplary techniques include making the residue obtained after separation and collection of the compound (1) come in contact with a solvent to extract the compound (2), thereby collecting the compound (2); separating and collecting the compound (1) by distillation, and the collecting the compound (2) by increasing the temperature and/or reducing the pressure; and making the residue obtained after separation and collection of the compound (1) come in contact with a solvent capable of dissolving the residue to prepare a solution, which is mixed with a solvent having a lower compatibility with the solution to extract the compound (2), thereby collecting the compound (2), for example.

The solvent capable of dissolving the residue obtained after separation and collection of the compound (1) is, but not particularly limited to, preferably a solvent having a hydroxyl group, and more preferably an alcohol such as methanol, ethanol, or propanol, or water, and even more preferably water. These solvents may be used alone or in a combination of two or more. Further, a compound soluble to these solvents may be added. Examples of the soluble compound include, but are not particularly limited to, sodium sulfate, sodium hydrogen sulfate, sodium phosphate, disodium hydrogen phosphate, sodium dihydrogen phosphate, sodium hydrogen carbonate, sodium carbonate, sodium chloride, potassium chloride, sodium nitrate, and potassium nitrate. These compounds may be used alone or in a combination of two or more.

Examples of the solvent having a lower compatibility to the solvent capable of dissolving the residue obtained after separation and collection of the compound (1) include, but are not particularly limited, aliphatic hydrocarbons such as pentane, hexane, and heptane; aromatic hydrocarbons such as benzene, toluene, xylene, hexafluorobenzene, and benzotrifluoride; ethers such as diethyl ether, diisopropyl ether, tert-butyl methyl ether, tetrahydrofuran, methyltetrahydrofuran, dimethoxyethane, cyclopentyl methyl ether, and 4-methyltetrahydropyran; and esters such as ethyl acetate and butyl acetate. Among these, ethers are preferred, and diethyl ether, diisopropyl ether, tert-butyl methyl ether, cyclopentyl methyl ether, and 4-methyltetrahydropyran are more preferred. These solvents may be used alone or in a combination of two or more.

<Step (b)>

The step (b) is a step of making a compound (1) come in contact and be mixed with a fluorinating agent to prepare a reaction mixture containing a compound (2) and a compound (3).

The process for producing a vinylsulfonyl fluoride of the present embodiment includes at least a step (b).

The compound (1) in the step (b) is preferably a compound (1) obtained by the above-mentioned process for producing a vinylsulfonic anhydride of this embodiment, and a compound obtained by the process for producing a vinylsulfonic anhydride may be continuously used in the step (b) or may be used in the step (b) after having been stored.

In the step (b), an additional compound may be included within a range not inhibiting the reaction. For example, the mixture of the compound (1) and the compound (2) obtained in the step (a) may be used.

Examples of the above-mentioned fluorinating agent include hydrogen fluoride, a metal fluoride, a quaternary ammonium fluoride, and a quaternary phosphonium fluoride, and at least one of hydrogen fluoride, a metal fluoride, a quaternary ammonium fluoride, and a quaternary phosphonium fluoride may be selected.

In the case where hydrogen fluoride is used as the fluorinating agent, a hydrogen fluoride may be subjected to the reaction alone or in the presence of an organic base. In the case where an organic base is used, the following can be used:

primary amines, such as methylamine, ethylamine, isopropylamine, and butylamine;

secondary amines, such as dimethylamine, diethylamine, diisopropylamine, and morpholine;

tertiary amines, such as trimethylamine, triethylamine, and diisopropylethylamine; and nitrogen-containing aromatic heterocyclic compounds, such as pyridine, 2,6-lutidine, imidazole, and quinoline.

These organic bases may be used alone or in a combination of two or more of organic bases.

In the case where a metal fluoride is used as the fluorinating agent, examples of the metal include alkali metals (Li, Na, K, Rb, and Cs), alkaline earth metals (Mg and Ca), and Ag. Specific examples of the metal fluoride include LiF, NaF, KF, RbF, CsF, $MgF_2$, $CaF_2$, and AgF. From the viewpoint of the reactivity with the compound (1), the fluorinating agent is more preferably at least one or more metal fluorides selected from the group consisting of LiF, NaF, KF, RbF, CsF, and AgF, and NaF and KF are particularly preferred.

In the case where a quaternary ammonium fluoride is used as the fluorinating agent, specific examples thereof include tetramethylammonium fluoride, tetraethylammonium fluoride, and tetrabutylammonium fluoride.

In the case where a quaternary phosphonium fluoride is used as the fluorinating agent, specific examples thereof include tetramethylphosphonium fluoride, tetraethylphosphonium fluoride, and tetrabutylphosphonium fluoride.

The above-mentioned fluorinating agents may be used alone or as a mixture of two or more.

The fluorinating agent is used in the step (b) in an amount of typically 0.95 to 20 mol with respect to 1 mol of the compound (1). Nevertheless, if any unused fluorinating agent would remain after the step (b), the unused fluorinating agent would remain together with the compound (2) after separation of the compound (3). Thus, it is desirable that the unused fluorinating agent remains as little as possible after the step (b). For this reason, the fluorinating agent is used in an amount of preferably from 0.98 to 10 mol, more preferably from 1 to 3 mol, and particularly preferably from 1 to 2 mol, with respect to 1 mol of the compound (1).

The step (b) may be carried out under a solvent-free condition or in the presence of a solvent.

In the case where the step (b) is carried out in the presence of a solvent, preferred solvents are solvents inert to the raw materials and the reaction products. Examples of the solvent include aliphatic hydrocarbons such as hexane and heptane; aromatic hydrocarbons such as benzene, toluene, and xylene; chlorinated hydrocarbons such as methylene chloride and chloroform; ethers such as diethyl ether, tetrahydrofuran, tert-butyl methyl ether, cyclopentyl methyl ether, 4-methyltetrahydropyran, monoglyme, diglyme, triglyme, and tetraglyme; ketones such as acetone and methyl ethyl ketone; esters such as ethyl acetate and butyl acetate; amides such as N,N-dimethylformamide, N,N-dimethylacetamide, and N-methylpyrrolidone; nitriles such as acetonitrile, propionitrile, butyronitrile, isobutyronitrile, and 2-methylbutyronitrile; dimethyl sulfoxide; and water. Among these, heptane, toluene, chloroform, monoglyme, diglyme, triglyme, tetraglyme, acetonitrile, propionitrile, butyronitrile, isobutyronitrile, 2-methylbutyronitrile, and water are preferred; acetonitrile, propionitrile, butyronitrile, isobutyronitrile, 2-methylbutyronitrile, and water are more preferred; and acetonitrile is particularly preferred. A solvent may be used alone, or two or more solvents may be used in a combination.

In the case where the step (b) is carried out in the presence of a solvent, the reaction temperature is typically −40° C. to 250° C. From the viewpoint of the thermal stabilities of the compound (1), the compound (2), and the compound (3) and the production rates of the compound (2) and the compound (3), the reaction temperature is preferably from −20° C. to 200° C., more preferably from 0° C. to 180° C., and particularly preferably from 10° C. to 150° C.

In the case where the step (b) is carried out in the presence of a solvent, the reaction time is typically 0.01 to 50 hours, and is preferably 0.1 to 30 hours.

In the case where the step (b) is carried out under a solvent-free condition, the reaction temperature is typically −40° C. to 300° C. From the viewpoint of the thermal stabilities of the compound (1), the compound (2), and the compound (3) and the production rates of the compound (2) and the compound (3), the reaction temperature is preferably from −20° C. to 280° C., more preferably from 0° C. to 250° C., and particularly preferably from 10° C. to 200° C.

In the case where the step (b) is carried out under a solvent-free condition, the reaction time is typically from 0.01 to 40 hours, and is preferably from 0.1 to 20 hours.

M in the compound (2) produced in the step (b) is a hydrogen atom, an alkali metal, an alkaline earth metal, Ag, a quaternary ammonium salt, or a quaternary phosphonium salt, and M can be appropriately modified according to the fluorinating agent described above. For example, in the case where a metal fluoride is used as the fluorinating agent, M in the compound (2) may be the same as the metal atom in that metal fluoride.

<Step (c)>

The step (c) is a step of separating the compound (3) from the reaction mixture containing the compound (3) and the compound (2) prepared in the above-mentioned step (b). Any techniques may be used to separate the compound (3) from the reaction mixture.

The process for producing a vinylsulfonyl fluoride of the present embodiment includes the step (b), and preferably also includes the step (c).

In the case where the reaction is carried out in the presence of a solvent in the step (b), for example, exemplary techniques of separating the compound (3) from the reaction mixture include the following:

adding water to the resultant reaction mixture, and separating the compound (3) an extraction solvent; and heating the resultant reaction mixture to separate the solvent and the compound (3) from each other by distillation.

In the case where an extraction solvent is used, preferred solvents are solvents which is insoluble to water, and is inert to the compound (3) and is capable of dissolving the compound (3). Example of the solvent include aliphatic hydrocarbons such as hexane and heptane; aromatic hydrocarbons such as benzene, toluene, and xylene; chlorinated hydrocarbons such as methylene chloride and chloroform; ethers such as diethyl ether, tert-butyl methyl ether, cyclopentyl methyl ether, and 4-methyltetrahydropyran; esters such as ethyl acetate and butyl acetate; and fluorine-based solvents such as HFC-4310mee, fluoroalkylsulfonic anhydrides $(C_mF_{2m+1}SO_2)_2O$ (m=1-10), fluoroalkylsulfonic acid esters $C_mF_{2m+1}SO_2OC_nF_{2n+1}$ (m=1 to 10 and n=1-10), perfluoroalkanes $C_mF_{2m+2}$ (m=4-20), perfluoroalkylamines $(C_mF_{2m+1})_3N$ (m=2-10), and perfluoropolyethers. The extraction solvents may be used alone or in a combination of two or more of solvents.

In the case the reaction is carried out under a solvent-free condition in the step (b), the technique for separating the compound (3) from the reaction mixture may be, for example, distilling out the compound (3) from the mixture during and/or after the reaction in the step (b) by distillation to thereby separate the compound (3).

The compound (3) separated in the above-mentioned step may be used as a fluorinated monomer as it is for copolymerization with TFE or other substances. Alternatively, the compound (3) may be used as a fluorinated monomer for copolymerization with TFE or other substances after the compound (3) is washed with water and optionally purified by distillation to increase the purity of the fluorinated monomer.

The compound (2) separated in the above-mentioned step can be converted to the compound (1) through the step (a), or can be converted to the compound (1) through the step (d) described below and further through the step (a).

<Step (d)>

The step (d) is a step of making a vinylsulfonic acid compound in which M in the general formula (2) is an alkali metal, an alkaline earth metal, Ag, a quaternary ammonium salt, or a quaternary phosphonium salt, come in contact and be mixed with an acidic substance, for conversion to a vinylsulfonic acid represented by the following general formula (4):

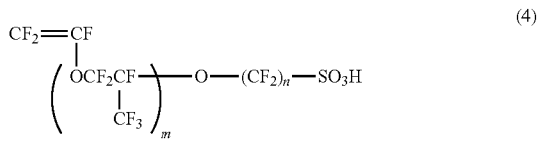

(where m and n are as defined in the general formula (2)).

The vinylsulfonic acid compound in the general formula (2) in which M is an alkali metal, an alkaline earth metal, Ag, a quaternary ammonium salt, or a quaternary phosphonium salt, may be subjected to the step (d), and the compound (4) produced in the step (d) can be used to produce the compound (1) in the step (a).

As the acidic substance, an inorganic acid such as hydrochloric acid, sulfuric acid, nitric acid, fuming sulfuric acid, phosphoric acid, or hydrogen bromide; or an organic acid such as methanesulfonic acid, benzenesulfonic acid, para-toluenesulfonic acid, trifluoromethanesulfonic acid, or perfluorobutanesulfonic acid; a strongly acidic ion-exchange resin; or the like may be made to come in contact and be mixed with the compound (2). These acidic substances may be used alone or in a combination of two or more.

The amount of the acidic substance used depends on the valence of the acid used, and the acidic substance may be used in an amount of 1 mol or more with respect to 1 mol of the compound (2).

In the step (d), the compound (2) may be converted to the compound (4) under a solvent-free condition, or the compound (2) may be converted to the compound (4) in the presence of a solvent.

In the case where the compound (2) is converted to the compound (4) in the presence of a solvent in the step (d), preferred solvents are solvents inert to the acidic substance. Preferred solvents include aliphatic hydrocarbons such as hexane and heptane; aromatic hydrocarbons such as benzene, toluene, and xylene; chlorinated hydrocarbons such as methylene chloride and chloroform; ethers such as diethyl ether, tert-butyl methyl ether, cyclopentyl methyl ether, 4-methyltetrahydropyran, monoglyme, diglyme, triglyme, and tetraglyme; esters such as ethyl acetate and butyl acetate; nitriles such as acetonitrile, propionitrile, butyronitrile, isobutyronitrile, and 2-methylbutyronitrile; and water. A solvent may be used alone, or two or more solvents may be used in a combination.

In the case where the step (d) is carried out in the presence of a solvent and the same solvent is used in the subsequent step (a), the remaining solvent may be used without being removed. In the case where a different solvent is used or the reaction is carried out under a solvent-free condition in the subsequent step (a), the solvent is preferably distilled off. The compound (4) with a high purity can be produced by subjecting the resultant compound (4) to distillation or the like.

In the case where the compound (2) is converted to the compound (4) under a solvent-free condition in the step (d), the compound (4) with a high purity can be produced by subjecting the resultant compound (4) to distillation or the like.

As described above, a synthesis by way of a vinylsulfonic anhydride produced from a vinylsulfonic acid compound and an anhydridization agent can enable an efficient production of a fluorinated monomer which may serve as a raw material of fluorine-based polymer electrolytes having a high heat resistance, such as membranes for fuel cells, catalyst binder polymers for fuel cells, and membranes for chlor-alkali electrolysis.

EXAMPLES

While the present disclosure will now be described in more details with reference to examples and comparative examples, it is understood that the present disclosure is not limited to these examples. The analytical and evaluation techniques used in examples and comparative examples are as follows:

Nuclear magnetic resonance analyses (NMR): molecular structure analyses by $^{19}$F-NMR Measurement apparatus: Avance 500 (available from Bruker Corporation)

Measurement tube: double-layered NMR tube (the outer tube contained deuterochloroform (reference material: CFCl$_3$ (0 ppm)) and the inner tube contained a sample (internal standard: hexafluorobenzene))

Accumulation count: 16 times

Gas chromatography (GC)

Measurement apparatus: GC-2010 Plus (available from Shimadzu Corporation)

Column: capillary column Rtx-200 available from Restek Corporation, USA (having an inner diameter of 0.25 mm, a length of 60 m, and a film thickness of 1 μm)

Carrier gas: helium

Carrier gas flow rate: 30 mL/min

Injection volume: 1 μL

Split ratio: 30

Vaporization chamber temperature: 200° C.

Program for column temperature: the temperature was kept at 40° C. for 10 min, raised at 20° C./min, and then kept at 280° C. for 10 min Detection: FID at 280° C.

Gas chromatography mass spectrum (GC-MS)

Measurement apparatus: GCMS-QP2020 (available from Shimadzu Corporation)

Column: capillary column Rtx-200 available from Restek Corporation, USA (having an inner diameter of 0.25 mm, a length of 60 m, and a film thickness of 1 μm)

Carrier gas: helium

Carrier gas flow rate: 30 mL/min

Injection volume: 1 μL

Split ratio: 30

Vaporization chamber temperature: 200° C.

Program for column temperature: the temperature was kept at 40° C. for 10 min, raised at 20° C./min, and then kept at 280° C. for 10 min Ion source: EI Example 1

Synthesis of $CF_2=CFOCF_2CF_2SO_3Na$ (Compound (2)) from $CF_3CF(COF)OCF_2CF_2SO_2F$ by Way of Cyclic Compound A 3-L round-bottomed flask equipped with a mechanical stirrer, a dropping funnel, and a reflux condenser was charged with sodium carbonate (328.6 g, 3.10 mol) which had been dried at 180° C. for 6 hours, and tetraglyme (1000 mL). While the temperature inside the reactor was kept 30° C. or lower, $CF_3CF(COF)OCF_2CF_2SO_2F$ (934.2 g, 2.70 mol) was added dropwise for more than 3 hours. After the dropwise addition completed, the reaction mixture was further stirred at 40° C. for 1 hour to yield a carboxylic acid sodium salt ($CF_3CF(CO_2Na)OCF_2CF_2SO_2F$). The resultant reaction mixture was heated at 160° C. under normal pressure to induce decarboxylation. A volatile component was distilled off, which was collected in an ice-cooled vessel. This colorless liquid was identified as the following cyclic compound (741.9 g, 2.65 mol; yield: 98%) by $^{19}$F-NMR.

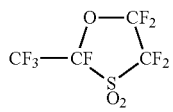

$^{19}$F-NMR: δ (ppm) −124.7 (1F), −120.6 (1F), −115.4 (1F), −90.1 (1F), −80.5 (3F), −78.0 (1F)

A 500-mL 4-necked flask under a nitrogen atmosphere was charged with the cyclic compound (20.39 g, 0.073 mol) produced in the above-mentioned step, and was cooled to 0° C. Next, a solution of sodium trimethylsilanolate (available from Sigma Aldrich Co., LLC; 16.03 g, 0.143 mol) dissolved in 4-methyltetrahydropyran (120.85 g) was added dropwise to this flask for 1 hour, followed by further stirring at room temperature for 2 hours. Vacuum concentration of the resultant reaction mixture gave a solid residue (28.7 g). This solid residue was identified to contain 70.0% by mass (yield: 92%) of $CF_2=CFOCF_2CF_2SO_3Na$ by $^{19}$F-NMR (internal standard: trifluoroethanol).

$CF_2=CFOCF_2CF_2SO_3Na$ $^{19}$F-NMR: δ (ppm) −136.3 (1F), −123.3 (1F), −118.8 (2F), −115.4 (1F), −85.4 (2F)

Synthesis of $CF_2=CFOCF_2CF_2SO_3H$ (Compound (4)) from $CF_2=CFOCF_2CF_2SO_3Na$ (Compound (2)) (Step (d))

A 300-ml four-neck flask was charged with $CF_2=CFOCF_2CF_2SO_3Na$ (70.02 g, 0.233 mol) and sulfuric acid (79.31 g, 0.79 mol) at room temperature, and the mixture was stirred at 70° C. while the pressure inside the flask was kept at 30 kPa. After a while, a uniform dissolution was achieved. Then, after the flask was gradually heated to a temperature of to 145° C. while the pressure inside the flask was reduced to 0.33 kPa, a liquid was distilled out (the amount obtained: 59.91 g). This liquid was identified as $CF_2=CFOCF_2CF_2SO_3H$ (0.216 mol, yield: 93%) by $^{19}$F-NMR.

Synthesis of $(CF_2=CFOCF_2CF_2SO_2)_2O$ (Compound (1)) from $CF_2=CFOCF_2CF_2SO_3H$ (Compound (4)) (Step (a))

A 300-mL four-necked flask was charged with phosphorus pentoxide ($P_2O_5$) (80.8 g, 0.569 mol) in a glove box in a dry air atmosphere. A Liebig condenser and a dropping funnel were attached to the flask, and the mixture was heated at 50° C. under a nitrogen stream. Then, after a vinylsulfonic acid ($CF_2=CFOCF_2CF_2SO_3H$) (79.13 g, 0.285 mol) was added dropwise from the dropping funnel, the flask was heated to 140° C. and the pressure inside the flask was changed from normal pressure to 60 kPa. After the flask was further heated to 160° C. and the pressure inside the flask was reduced to 20 kPa, a liquid was distilled out (63.53 g). This liquid was identified to contain 90% by mass (0.106 mol, yield: 74%) of $(CF_2=CFOCF_2CF_2SO_2)_2O$ and 10% by mass (0.023 mol) of $CF_2=CFOCF_2CF_2SO_3H$ by $^{19}$F-NMR.

$(CF_2=CFOCF_2CF_2SO_2)_2O$ $^{19}$F-NMR: δ (ppm) −138.6 (2F), −123.3 (2F), −116.0 (2F), −111.9 (4F), −84.6 (4F)

EI-MS: m/z 261, 194, 169, 147, 131, 119, 100, 97, 81, 69, 50, 47, 31

Synthesis of $CF_2=CFOCF_2CF_2SO_2F$ (Compound (3)) and $CF_2=CFOCF_2CF_2SO_3Na$ (Compound (2)) from $(CF_2=CFOCF_2CF_2SO_2)_2O$ (Compound (1)) and NaF (Steps (b) and (c))

NaF (5.26 g, 0.125 mol) was weighed in a 100-mL three-necked flask and then dried under vacuum at 150° C. for 1 hour, and the flask was returned to the normal pressure and room temperature condition. A Liebig condenser and a dropping funnel were attached to the flask. A mixture (44.92 g) of $(CF_2=CFOCF_2CF_2SO_2)_2O$ and $CF_2=CFOCF_2CF_2SO_3H$ (a mixture of 96% by weight (0.080 mol) of $(CF_2=CFOCF_2CF_2SO_2)_2O$ and 4% by weight (0.0065 mol) of $CF_2=CFOCF_2CF_2SO_3H$) was added dropwise from the dropping funnel at room temperature under a nitrogen stream. Then, after the flask was heated to 190° C. under a reduced pressure (95 kPa), a liquid was distilled out (17.56 g). This liquid was identified as $CF_2=CFOCF_2CF_2SO_2F$ (0.063 mol) by $^{19}$F-NMR. Further, the residue (31.17 g) in the distillation still was identified to contain 94.56% by mass (0.098 mol) of $CF_2=CFOCF_2CF_2SO_3Na$, 0.27% by mass (0.00015 mol) of $(CF_2=CFOCF_2CF_2SO_2)_2O$, and 5.17% by mass (0.038 mol) of NaF by $^{19}$F-NMR, which was carried out by adding acetonitrile and hexafluorobenzene (internal standard) to the residue.

Synthesis of $CF_2=CFOCF_2CF_2SO_3H$ (Compound (4)) from $CF_2=CFOCF_2CF_2SO_3Na$ (Compound (2)) Produced in the Above-Mentioned Step (c) (Step (d))

A strongly acidic cation exchange resin IR120B (available from ORGANO CORPORATION) (93 ml, 0.184 eq.) was washed with a 1-N water solution of sulfuric acid (1000 mL) and then further washed with deionized water (1000 mL). Deionized water (265.5 g) was added to the residue (29.50 g) in the distillation still obtained in above-mentioned step (which contained 94.56% by mass (0.093 mol) of $CF_2=CFOCF_2CF_2SO_3Na$, 0.27% by mass (0.00015 mol) of $(CF_2=CFOCF_2CF_2SO_2)_2O$, and 5.17% by mass (0.036 mol) of NaF) to prepare a water solution, which was then allowed to flow through the strongly acidic cation exchange resin. Further, after deionized water (214 g) was further allowed to flow through the cation exchange resin, the collected water solution (509 g) was concentrated under a reduced pressure to yield 31.50 g of a liquid. This liquid was identified to contain 78% by mass (0.088 mol, yield: 95%) of $CF_2=CFOCF_2CF_2SO_3H$ by $^{19}$F-NMR. Further, distillation of the liquid under a reduced pressure (0.33 kPa) gave 23.20 g of $CF_2=CFOCF_2CF_2SO_3H$.

Synthesis of $(CF_2=CFOCF_2CF_2SO_2)_2O$ (Compound (1)) from $CF_2=CFOCF_2CF_2SO_3H$ (Compound (4)) Produced in the Above-Mentioned Step (d) (Step (a))

A 200-mL four-necked flask was charged with phosphorus pentoxide ($P_2O_5$) (24.97 g, 0.176 mol) in a glove box in a dry air atmosphere. A Liebig condenser and a dropping funnel were attached to the flask, and the mixture was heated at 50° C. under a nitrogen stream. Then, after $CF_2=CFOCF_2CF_2SO_3H$ (16.42 g, 0.059 mol) obtained in the above-mentioned step (d) was added dropwise from the dropping funnel, the flask was heated to 140° C. and the pressure inside the flask was changed from normal pressure to 60 kPa. After the flask was further heated to 160° C. and the pressure inside the flask was reduced to 20 kPa, a liquid was distilled out (11.35 g). This liquid was identified to contain 95% by mass (0.020 mol, yield: 68%) of $(CF_2=CFOCF_2CF_2SO_2)_2O$ and 5% by mass (0.0021 mol) of $CF_2=CFOCF_2CF_2SO_3H$ by $^{19}$F-NMR.

Example 2

Synthesis of $(CF_2=CFOCF_2CF_2SO_2)_2O$ (Compound (1)) from $CF_2=CFOCF_2CF_2SO_3Na$ (Compound (2)) by Way of $CF_2=CFOCF_2CF_2SO_3H$ (Compound (4)) (Steps (d) and (a))

A strongly acidic cation exchange resin IR120B (available from ORGANO CORPORATION) (357 ml, 0.714 eq.) was washed with a 1-N water solution of sulfuric acid (3570 mL) and then further washed with deionized water (3570 mL). A water solution of 10% by weight of $CF_2=CFOCF_2CF_2SO_3Na$ (1500 g, 0.50 mol) was allowed to flow through the cation exchange resin, and deionized water (524 g) was then allowed to flow through. Concentration of the collected water solution gave a liquid (143 g). This liquid was identified to contain 93.8% by mass (0.48 mol, yield: 96%) of $CF_2=CFOCF_2CF_2SO_3H$ by $^{19}$F-NMR (internal standard: benzotrifluoride).

A 1000-mL four-necked flask was charged with phosphorus pentoxide ($P_2O_5$) (217.3 g, 1.531 mol) in a glove box in a dry air atmosphere. A Liebig condenser and a dropping funnel were attached to the flask, and the mixture was heated at 50° C. under a nitrogen stream. Then, after the above-mentioned concentrate (143 g) was added dropwise from the dropping funnel, the flask was heated to 140° C. and the pressure inside the flask was changed from normal pressure to 60 kPa. After the flask was further heated to 160° C. and the pressure inside the flask was reduced to 20 kPa, a liquid was distilled out (104.7 g). This liquid was identified to contain 90% by mass (0.18 mol, yield: 70%) of $(CF_2=CFOCF_2CF_2SO_2)_2O$ and 9% by mass (0.034 mol) of $CF_2=CFOCF_2CF_2SO_3H$ by $^{19}$F-NMR.

Example 3

Synthesis of $(CF_2=CFOCF_2CF_2SO_2)_2O$ (Compound (1)) from $CF_2=CFOCF_2CF_2SO_3Na$ (Compound (2)) by Way of $CF_2=CFOCF_2CF_2SO_3H$ (Compound (4)) (Steps (d) and (a))

To $CF_2=CFOCF_2CF_2SO_3Na$ (300 g, 1 mol), 30% by weight of a water solution of sulfuric acid (490 g) was added, and the mixture was then stirred at room temperature. Cyclopentyl methyl ether (CPME) (1500 g) was further added, followed by stirring at room temperature for 1 hour. After the mixture was left to stand after the stirring was stopped, the mixture separated into two layers. After the organic layer was isolated and then concentrated under a reduced pressure, a liquid (291.0 g) was obtained. This liquid was identified to contain 93.6% by mass (0.98 mol, yield: 98%) of $CF_2=CFOCF_2CF_2SO_3H$ by $^{19}$F-NMR (internal standard: benzotrifluoride).

A 2000-mL four-necked flask was charged with phosphorus pentoxide ($P_2O_5$) (442.4 g, 3.117 mol) in a glove box in a dry air atmosphere. A Liebig condenser and a dropping funnel were attached to the flask, and the mixture was heated at 50° C. under a nitrogen stream. Then, after the above-mentioned concentrate (291.0 g) was added dropwise from the dropping funnel, the flask was heated to 140° C. and the pressure inside the flask was changed from normal pressure to 60 kPa. After the flask was further heated to 160° C. and the pressure inside the flask was reduced to 20 kPa, a liquid was distilled out (213.2 g). This liquid was identified to contain 90% by mass (0.36 mol, yield: 71%) of $(CF_2=CFOCF_2CF_2SO_2)_2O$ and 9% by mass (0.07 mol) of $CF_2=CFOCF_2CF_2SO_3H$ by $^{19}$F-NMR.

Example 4

Synthesis of $CF_2=CFOCF_2CF_2SO_2F$ (Compound (3)) and $CF_2=CFOCF_2CF_2SO_3K$ (Compound (2)) from $(CF_2=CFOCF_2CF_2SO_2)_2O$ (Compound (1)) and KF (Steps (b) and (c))

KF (2.60 g, 0.045 mol) was weighed in a 100-mL three-necked flask and then dried under vacuum at 150° C. for 1 hour, and the flask was returned to the normal pressure and room temperature condition. A Liebig condenser and a dropping funnel were attached to the flask. A mixture (14.25 g) of $(CF_2=CFOCF_2CF_2SO_2)_2O$ and $CF_2=CFOCF_2CF_2SO_3H$ (a mixture of 88% by weight (0.023 mol) of $(CF_2=CFOCF_2CF_2SO_2)_2O$ and 12% by weight (0.006 mol) of $CF_2=CFOCF_2CF_2SO_3H$) was added dropwise from the dropping funnel at room temperature under a nitrogen stream. Then, after the flask was heated to 110° C. under a reduced pressure (90 kPa), a liquid was distilled out (6.30 g). This liquid was identified to contain 92% by mass (0.017 mol) of $CF_2=CFOCF_2CF_2SO_2F$ and 0.4% by mass (0.000045 mol) of $(CF_2=CFOCF_2CF_2SO_2)_2O$ by $^{19}$F-NMR. Further, the residue (10.80 g) in the distillation still was identified to contain 87% by weight (0.030 mol) of $CF_2=CFOCF_2CF_2SO_3K$ by $^{19}$F-NMR, which was carried out by adding acetonitrile and hexafluorobenzene (internal standard) to the residue.

Example 5

Synthesis of $CF_2=CFOCF_2CF_2SO_2F$ (Compound (3)) and $CF_2=CFOCF_2CF_2SO_3Na$ (Compound (2)) from $(CF_2=CFOCF_2CF_2SO_2)_2O$ (Compound (1)) and NaF (Step (b))

$(CF_2=CFOCF_2CF_2SO_2)_2O$ (0.66 g, 0.00123 mol), NaF (0.083 g, 0.0020 mol, and acetonitrile (2.8 g) were placed in a 50-ml screw top test tube, and allowed to react at 40° C. for 1 hour. The resultant reaction mixture was identified to contain $CF_2=CFOCF_2CF_2SO_2F$ (0.00074 mol) and $CF_2=CFOCF_2CF_2SO_3Na$ (0.0016 mol) by $^{19}$F-NMR.

Example 6

Synthesis of $CF_2=CFOCF_2CF_2SO_2F$ (Compound (3)) and $CF_2=CFOCF_2CF_2SO_3K$ (Compound (2)) from $(CF_2=CFOCF_2CF_2SO_2)_2O$ (Compound (1)) and KF (Step (b))

$(CF_2=CFOCF_2CF_2SO_2)_2O$ (0.69 g, 0.00128 mol), KF (0.11 g, 0.0019 mol), and acetonitrile (2.9 g) were placed in a 50-ml screw top test tube, and allowed to react at 40° C. for 1 hour. The resultant reaction mixture was identified to contain $CF_2=CFOCF_2CF_2SO_2F$ (0.00082 mol) and $CF_2=CFOCF_2CF_2SO_3K$ (0.0017 mol) by $^{19}$F-NMR.

Example 7

In the synthesis of $(CF_2=CFOCF_2CF_2SO_2)_2O$ (compound (1)) from $CF_2=CFOCF_2CF_2SO_3H$ (compound (4)) in Example 1, after the liquid was distilled off, the remained residue (10 g) was added to a solution containing sodium carbonate (12.7 g) and water (57.9 g), followed by stirring. Further, 4-methyltetrahydropyran (40.3 g) was added, followed by further stirring. After the mixture was left to stand after the stirring was stopped, the mixture separated into two layers. After the 4-methyltetrahydropyran layer was isolated and concentrated under a reduced pressure, a solid (0.792 g) was obtained. This solid was identified to contain 98% by mass (0.00259 mol) of $CF_2=CFOCF_2CF_2SO_3Na$ by $^{19}$F-NMR (internal standard: benzotrifluoride).

Example 8

Synthesis of $(CF_2=CFOCF_2CF_2SO_2)_2O$ (Compound (1)) from $CF_2=CFOCF_2CF_2SO_3Na$ (Compound (2)) and Phosphorus Pentoxide ($P_2O_5$) (Step (a))

Phosphorus pentoxide ($P_2O_5$) (94.6 g, 0.666 mol) and a vinylsulfonic acid salt ($CF_2=CFOCF_2CF_2SO_3Na$) (100 g, 0.333 mol) were placed in a mini speed mill (MS-05 available from Labonect Co. Ltd.), and stirred for 30 minutes to prepare a mixture. The resultant mixture was placed in a 500-mL four-necked flask. A Liebig condenser was attached to the flask, and the pressure was reduced to 0.3 kPa. After the flask was gradually heated to 200° C., a liquid was distilled out. The flask was kept at 200° C. for 45 minutes. The resultant liquid weighted 17.9 g. This liquid was identified to contain 95% by mass (0.0317 mol) of $(CF_2=CFOCF_2CF_2SO_2)_2O$ by $^{19}$F-NMR.

Example 9

Synthesis of $(CF_2=CFOCF_2CF_2SO_2)_2O$ (Compound (1)) from $CF_2=CFOCF_2CF_2SO_3Na$ (Compound (2)) and Phosphorus Pentoxide ($P_2O_5$) (Step (a))

Phosphorus pentoxide ($P_2O_5$) (9.72 g, 0.0685 mol), a vinylsulfonic acid salt ($CF_2=CFOCF_2CF_2SO_3Na$) (10.3 g, 0.0342 mol), and zirconia beads having a diameter of 1 mm (200 g, YTZ-1 available from Nikkato Corporation) were placed in a Teflon (Registered trademark) container. The container was placed in a low frequency resonant acoustic mixer (LabRAMII available from Resodyn Acoustic Mixers) and was processed at an acceleration of 100 G for 25 minutes to obtain a processed product. The processed product was filtrated through a 140 mesh sieve to yield a mixture of phosphorus pentoxide ($P_2O_5$) and the vinylsulfonic acid salt ($CF_2=CFOCF_2CF_2SO_3Na$). This procedure was repeated multiple times to obtain 50 g of the mixture. The resultant mixture was placed in a 200-mL three-necked flask. A Liebig condenser was attached to the flask, and the pressure was reduced to 0.3 kPa. After the flask was gradually heated to 200° C., a liquid was distilled out. The flask was kept at 200° C. for 45 minutes. The resultant liquid weighted 9.68 g. This liquid was identified to contain 95% by mass (0.0171 mol) of $(CF_2=CFOCF_2CF_2SO_2)_2O$ by $^{19}$F-NMR.

Example 10

In the synthesis of $(CF_2=CFOCF_2CF_2SO_2)_2O$ (compound (1)) from $CF_2=CFOCF_2CF_2SO_3Na$ (compound (2)) and phosphorus pentoxide ($P_2O_5$) in Example 9, after the liquid was distilled off, the remained residue (10 g) was added to a solution containing sodium carbonate (4.50 g) and water (20.5 g), followed by stirring. Further, 4-methyltetrahydropyran (17.5 g) was added, followed by further stirring. After the mixture was left to stand after the stirring was stopped, the mixture separated into two layers. After the 4-methyltetrahydropyran layer was isolated and concentrated under a reduced pressure, a solid (2.59 g) was obtained. This solid was identified to contain 98% by mass (0.00845 mol) of $CF_2=CFOCF_2CF_2SO_3Na$ by $^{19}$F-NMR (internal standard: benzotrifluoride).

INDUSTRIAL APPLICABILITY

According to the present disclosure, a fluorinated monomer can be produced in a good yield, which is a raw material of fluorine-based polymer electrolytes having high heat resistances useful for applications, such as membranes for fuel cells, catalyst binder polymers for fuel cells, and membranes for chlor-alkali electrolysis.

The invention claimed is:

1. A vinylsulfonic anhydride of general formula (1):

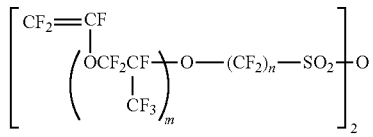
(1)

where m is an integer from 0 to 3, and n is an integer from 1 to 6.

2. A process for producing a vinylsulfonic anhydride of general formula (1):

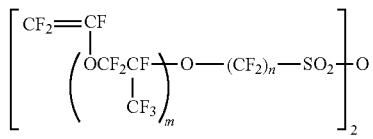
(1)

where m is an integer from 0 to 3, and n is an integer from 1 to 6,
the process comprising:
a step (a) of mixing a vinylsulfonic acid compound of general formula (2) with an anhydridization agent:

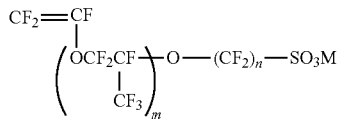
(2)

where m represents an integer from 0 to 3, n represents an integer from 1 to 6, and M represents a hydrogen atom, an alkali metal, an alkaline earth metal, Ag, a quaternary ammonium salt, or a quaternary phosphonium salt,
wherein the step (a) comprising a step of separating the vinylsulfonic anhydride of general formula (1).

3. A process for producing a vinylsulfonyl fluoride comprising:
a step (b) of mixing a vinylsulfonic anhydride of general formula (1) with a fluorinating agent:

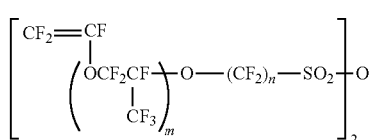
(1)

where m is an integer from 0 to 3, and n is an integer from 1 to 6,
to prepare a reaction mixture comprising a vinylsulfonyl fluoride of general formula (3):

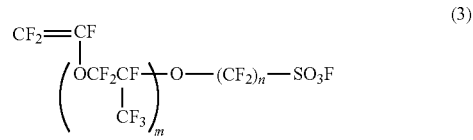
(3)

where m is an integer from 0 to 3, and n is an integer from 1 to 6; and
a vinylsulfonic acid compound of general formula (2):

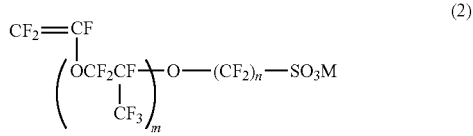
(2)

where m represents an integer from 0 to 3, n represents an integer from 1 to 6, and M represents a hydrogen atom, an alkali metal, an alkaline earth metal, Ag, a quaternary ammonium salt, or a quaternary phosphonium salt, and
a step (c) of separating the vinylsulfonyl fluoride of general formula (3) and the vinylsulfonic acid compound of general formula (2), from the reaction mixture prepared in the step (b).

4. The process for producing a vinylsulfonyl fluoride according to claim 3, wherein the vinylsulfonic anhydride is produced by the process for producing a vinylsulfonic anhydride of general formula (1):

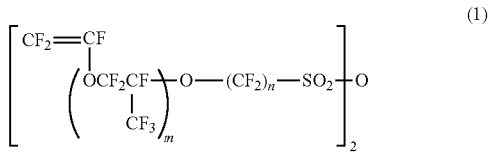
(1)

where m is an integer from 0 to 3, and n is an integer from 1 to 6,
the process comprising:
a step (a) of mixing a vinylsulfonic acid compound of general formula (2) with an anhydridization agent:

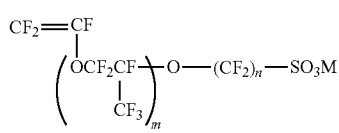
(2)

where m represents an integer from 0 to 3, n represents an integer from 1 to 6, and M represents a hydrogen atom, an alkali metal, an alkaline earth metal, Ag, a quaternary ammonium salt, or a quaternary phosphonium salt.

5. The process for producing a vinylsulfonic anhydride according to claim 2, wherein the step (a) comprises mixing the anhydridization agent with the vinylsulfonic acid compound of general formula (2) obtained in the step (c) of separating the vinylsulfonyl fluoride of the general formula (3) and the vinylsulfonic acid compound of general formula (2), from the reaction mixture prepared in the step (b) of mixing a vinylsulfonic anhydride of general formula (1) with a fluorinating agent:

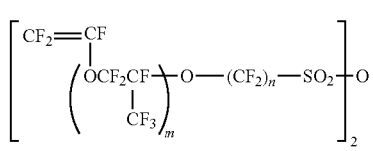

(1)

where m is an integer from 0 to 3, and n is an integer from 1 to 6 to prepare a reaction mixture comprising a vinylsulfonyl fluoride of general formula (3):

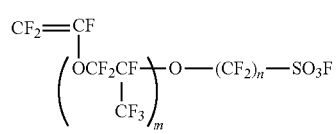

(3)

where m is an integer from 0 to 3, and n is an integer from 1 to 6; and a vinylsulfonic acid compound of general formula (2):

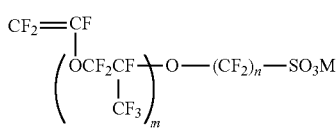

(2)

where m represents an integer from 0 to 3, n represents an integer from 1 to 6, and M represents a hydrogen atom, an alkali metal, an alkaline earth metal, Ag, a quaternary ammonium salt, or a quaternary phosphonium salt.

6. The process for producing a vinylsulfonic anhydride according to claim 2, further comprising a step (d) of mixing an acidic substance with a vinylsulfonic acid compound of general formula:

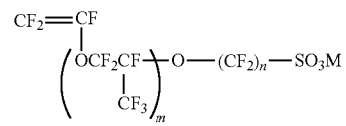

where m represents an integer from 0 to 3, n represents an integer from 1 to 6, and M represents an alkali metal, an alkaline earth metal, Ag, a quaternary ammonium salt, or a quaternary phosphonium salt, to prepare the vinylsulfonic acid compound of general formula (4):

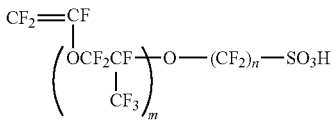

(4)

that is used in the step (a).

7. The process for producing a vinylsulfonyl fluoride according to claim 3, wherein the fluorinating agent is one or more selected from the group consisting of hydrogen fluoride, a metal fluoride, a quaternary ammonium fluoride, and a quaternary phosphonium fluoride.

8. The process for producing a vinylsulfonic anhydride according to claim 2, wherein the anhydridization agent is one or more selected from the group consisting of phosphorus pentoxide, acetic anhydride, trifluoroacetic anhydride, methanesulfonic anhydride, trifluoromethanesulfonic anhydride, p-toluenesulfonic anhydride, thionyl chloride, dicyclohexylcarbodiimide, cyanuric chloride, titanium tetrachloride, and benzenesulfonyl chloride.

9. The process for producing a vinylsulfonic anhydride according to claim 2, further comprising a step of, after separating the vinylsulfonic anhydride of general formula (1), collecting the vinylsulfonic acid compound of general formula (2) from a resultant residue.

10. The process for producing a vinylsulfonyl fluoride according to claim 2, wherein m is 0, and n is 2.

* * * * *